United States Patent [19]

Holtkamp

[11] Plant 4,374

[45] Feb. 6, 1979

[54] AFRICAN VIOLET PLANT

[75] Inventor: Reinhold Holtkamp, Isselburg, Fed. Rep. of Germany

[73] Assignee: Gessellschaftsvertrag uber die Erfindergemeinschaft "OPTIMARA", Isselburg, Fed. Rep. of Germany

[21] Appl. No.: 911,297

[22] Filed: May 31, 1978

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Donald D. Jeffery

[57] ABSTRACT

An African Violet known by the cultivar name Arizona, characterized by dark green leaves and strong upright peduncles each of which carries 10–12 individual flowers; generally red-purple flower color, with a tendency toward lighter streaking in the petals extending generally radially in the petal from the center of the flower, with the flowers being non-dropping, and having a prolific flowering characteristic which provides a full and tight bouquet above the foliage.

1 Drawing Figure

The present invention comprises a new and distinct cultivar of African Violet plant, botanically known as *Saintpaulia ionantha,* hereinafter referred to by the cultivar name Arizona. Arizona is the product of a plant breeding program, and was referred to during the breeding and selection process by the number designation 87/78.

The new cultivar was originated from a cross made in a controlled breeding program in Isselburg, Rhineland, Germany. The female, or seed parent, was an unpatented cultivar identified as FIII Pink (43-1). The male, or pollen parent, is also unpatented and identified as 4001 red (45-13). Arizona was discovered and selected as a flowering plant within the progeny of the stated cross by me in a controlled environment in Isselburg, Rhineland, Germany. Asexual reproduction of the new cultivar by leaf cuttings and by division of shoots, as performed by me at Isselburg, Rhineland, Germany, has demonstrated that the combination of characteristics as herein disclosed for the new cultivar are firmly fixed and are retained through successive generations of asexual reproduction.

The following characteristics have been repeatedly observed and are determined to be the basic characteristics of the new cultivar Arizona, which in combination distinguish this African Violet as a new and distinct cultivar;

1. Typical violet shaped blossoms or flowers.
2. The flowers are non-dropping, thereby reducing problems due to botrytis.
3. The pedicels are very straight and rigid, thereby providing an excellent bouquet of flowers above the foliage.
4. The flowers are of generally lilac-purple color, with several light stripes appearing in the flowers, generally extending radially from the center of the flower.
5. Dark green leaves.
6. There are as many as 10–12 individual flowers on each flower stem.

The accompanying photographic drawing comprises a perspective view of a typical specimen plant of the new cultivar. The colors appearing in the photograph are as true as possible with color illustration of this type.

In the following description, measurements, values and observations are made based on plants grown in Isselburg, Rhineland, Germany, under greenhouse conditions which closely approximate those generally used in commercial practice. Color references are made to the Royal Horticultural Society Color Chart (RHS), 1966 edition, except where general color terms of ordinary significance are used.

Botanical classification: *Saintpaulia ionantha,* Ramat. cv. Arizona.

Parentage:

*Male parent.*—4001 red (45-13).

*Female parent.*—FIII Pink (43-1).

Propagation: The new cultivar holds its distinguishing characteristics through successive propagations by leaf cuttings and by division of shoots.

Plant: The plant is from 8 cm. to 9 cm. tall when grown in pots, and approximately 25 cm. in diameter when fully grown.

Leaves:

*General form.*—Oval to round.

*Diameter.*—70–80 mm.

*Texture.*—soft, slightly hairy.

*Aspect.*—Edges are irregular in shape and serrated in certain areas.

*Veins.*—Well developed, light green in color.

*Color.*—(upperside) Dark green, 139A; due to reflection of leaves in photograph, color appears somewhat darker than true color values.

*Color.*—(underside) Dark purple, 187A.

*Petiole.*—Rigid, reddish-green in color.

Flowers:

*Buds.*—Round, diameter 7–8 mm. before blooming.

*Sepals.*—Five; 5–6 mm. long, spear-shaped. Color: reddish brown. Calyx: grown together with receptacle and seed-bud. Aspect: funnel shaped. Peduncle: Straight, wiry, 15–20 mm.

Individual Flowers:

*Size.*—The flower is up to 40 mm. in diameter, generally symmetrical in overall appearance.

*Color.*—Upperside: Red-purple, 64 A-C, with occasional lighter streaks extending radially in petal from center of flower. Underside: 64 B-D.

*Borne.*—The flower stems carry up to twelve single flowers, providing very prolific flowering.

*Shape.*—Five petals generally violet-shaped, two large petals approximately 24 mm. long and 17 mm. wide, and two smaller petals 10 mm. long and 11 mm. wide.

*Arrangement.*—Flowers are on strong, upright pedicels, up to twelve of which are carried on the peduncle.

*Flowering time.*—7–8 weeks after potting, the first flowers appear; after 10–12 weeks, the plant is in full bloom.

Reproductive organs:

*Stamens.*—Two in number.

*Anthers.*—4 anthers, close together, color 7 B.

*Arrangement.*—The stamens are connected to the receptacle by two short stems.

*Filaments.*—3–4 mm. long, flat, wide.

*Styles.*—7–8 mm. long.

*Pollen color.*—7 C.

Roots: The young plants have well developed and branched root system; young root tips are white, turning brownish when older.

Disease Resistance: No disease problems noticed to date.

General observations:

Arizona is a vigorous growing African Violet having an abundance of individual blossoms which provide a very prolific flowering characteristic. There are up to twelve individual blossoms on a single peduncle, all of which are very straight and wiry. Initial flowering occurs approximately 7–8 weeks after potting, and the plant is in full bloom 10–12 weeks after potting. The flowers are very durable and non-dropping, and provide a full and tight bouquet above the foliage.

I claim:

1. A new and distinct cultivar of African Violet plant characterized by the combined characteristics of dark green leaves and strong upright peduncles each of which carries 10–12 individual flowers; generally red-purple flower color, with a tendency toward lighter streaking in the petals extending generally radially in the petal from the center of the flower, with the flowers being non-dropping and comprised of three relatively larger petals and two relatively smaller petals which together form a generally symmetrical flower appearance, and by its prolific flowering characteristic which provides a full and tight bouquet above the foliage.

* * * * *

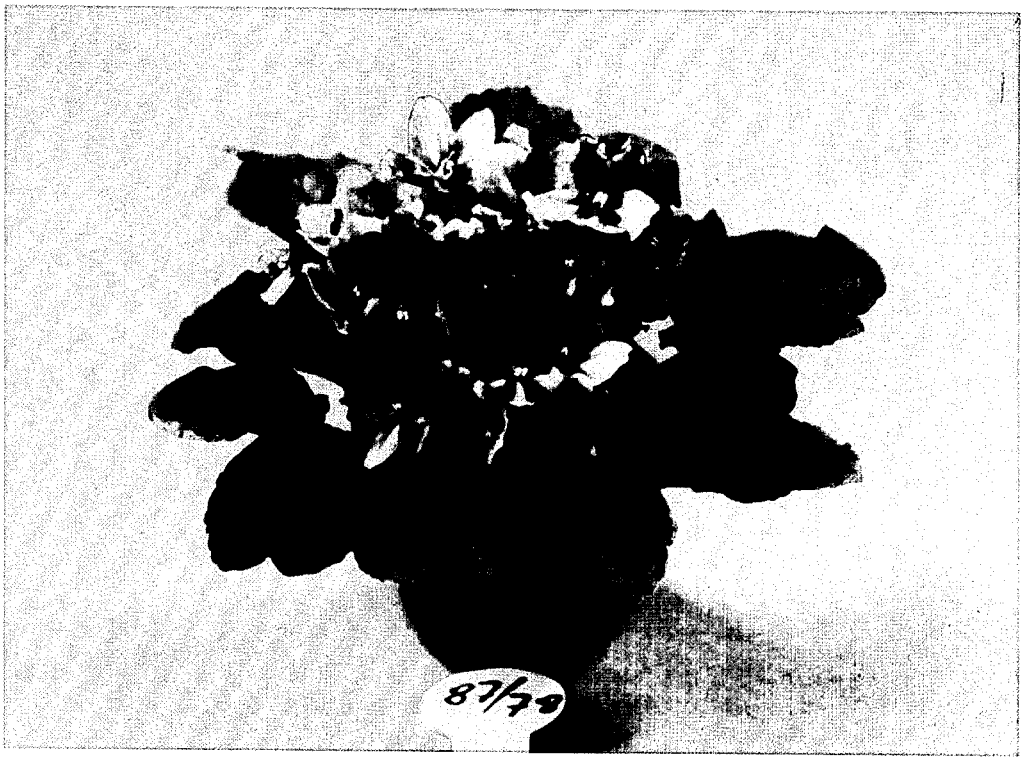
87/79